(12) United States Patent
Lepez et al.

(10) Patent No.: US 10,670,264 B2
(45) Date of Patent: Jun. 2, 2020

(54) CRACKING FURNACE

(71) Applicant: E.T.I.A.—EVALUATION TECHNOLOGIQUE, INGENIERIE ET APPLICATIONS, Compiegne (FR)

(72) Inventors: Olivier Lepez, Lamorlaye (FR); Philippe Sajet, Lacroix-Saint-Ouen (FR)

(73) Assignee: E.T.I.A.—EVALUATION TECHNOLOGIQUE, INGENIERIE ET APPLICATIONS, Compiegne (FR)

( * ) Notice: Subject to any disclaimer, the term of this patent is extended or adjusted under 35 U.S.C. 154(b) by 6 days.

(21) Appl. No.: 15/572,427

(22) PCT Filed: May 31, 2016

(86) PCT No.: PCT/EP2016/062311
§ 371 (c)(1),
(2) Date: Nov. 7, 2017

(87) PCT Pub. No.: WO2016/193274
PCT Pub. Date: Dec. 8, 2016

(65) Prior Publication Data
US 2018/0135854 A1    May 17, 2018

(30) Foreign Application Priority Data

Jun. 5, 2015 (FR) ..................................... 15 55148
Sep. 15, 2015 (FR) ..................................... 15 58609

(51) Int. Cl.
*F23G 5/027* (2006.01)
*F23C 3/00* (2006.01)
(Continued)

(52) U.S. Cl.
CPC ......... *F23G 5/0273* (2013.01); *B01D 53/047* (2013.01); *B01D 53/229* (2013.01);
(Continued)

(58) Field of Classification Search
CPC .................................................... F23G 5/0273
See application file for complete search history.

(56) References Cited

U.S. PATENT DOCUMENTS 2,255,540 A * 9/1941 Dreffein ............... C21D 9/0006
126/91 A
3,617,038 A * 11/1971 Schmidt ................... C01F 7/50
126/91 A
(Continued)

FOREIGN PATENT DOCUMENTS

EP    2 690 162 A1    1/2014
FR    2 774 545 A1    8/1999
WO    WO 2004/059208 A2    7/2004

*Primary Examiner* — Nathaniel Herzfeld
(74) *Attorney, Agent, or Firm* — Muncy, Geissler, Olds & Lowe, P.C.

(57) ABSTRACT

The invention relates to a cracking furnace containing a tubular vertical chamber which comprises an inlet for introducing a gas to be treated and an outlet for removing said gas from the chamber, means for heating said gas which include a heating tube extending vertically inside the chamber and coaxial with the chamber, the heating tube being shaped in such a way as to have a closed lower end and being arranged in such a way that the lower end thereof is arranged in the chamber and such that the upper end thereof is connected to a burner of the heating means arranged outside the chamber. The invention also relates to an assembly comprising such a cracking furnace and a device for thermal treatment of biomass and/or waste, an outlet of which is connected to the inlet of said cracking furnace.

31 Claims, 1 Drawing Sheet

(51) Int. Cl.
*F23G 5/10* (2006.01)
*F23G 5/24* (2006.01)
*F23G 7/06* (2006.01)
*H05B 3/40* (2006.01)
*F23C 99/00* (2006.01)
*F23G 5/12* (2006.01)
*F23G 7/10* (2006.01)
*B01D 53/047* (2006.01)
*B01D 53/22* (2006.01)
*B01D 53/26* (2006.01)
*C07C 4/02* (2006.01)
*C10B 5/00* (2006.01)
*C10B 7/10* (2006.01)
*C10B 19/00* (2006.01)
*C10B 27/06* (2006.01)
*C10B 47/44* (2006.01)
*C10B 53/07* (2006.01)
*F23G 5/44* (2006.01)

(52) U.S. Cl.
CPC ............. *B01D 53/265* (2013.01); *C07C 4/02* (2013.01); *C10B 5/00* (2013.01); *C10B 7/10* (2013.01); *C10B 19/00* (2013.01); *C10B 27/06* (2013.01); *C10B 47/44* (2013.01); *C10B 53/07* (2013.01); *F23C 3/002* (2013.01); *F23C 3/004* (2013.01); *F23C 99/00* (2013.01); *F23G 5/10* (2013.01); *F23G 5/12* (2013.01); *F23G 5/24* (2013.01); *F23G 5/444* (2013.01); *F23G 7/06* (2013.01); *F23G 7/063* (2013.01); *F23G 7/10* (2013.01); *H05B 3/40* (2013.01); *B01D 2256/245* (2013.01); *B01D 2257/102* (2013.01); *B01D 2257/504* (2013.01); *F23G 2203/30* (2013.01); *F23G 2205/10* (2013.01); *F23G 2900/50201* (2013.01); *F23M 2900/05004* (2013.01)

(56) References Cited

U.S. PATENT DOCUMENTS

| | | | | |
|---|---|---|---|---|
| 4,218,211 A | * | 8/1980 | Caplan | F23C 3/002 126/91 A |
| 5,554,347 A | * | 9/1996 | Busson | B01J 12/007 165/142 |
| 6,312,652 B1 | * | 11/2001 | Duncan | B01J 8/062 422/201 |
| 6,648,932 B1 | * | 11/2003 | Maton | C10B 47/22 48/119 |
| 2006/0199127 A1 | * | 9/2006 | Butler | F23C 3/002 431/215 |
| 2007/0266633 A1 | | 11/2007 | Tsangaris et al. | |
| 2009/0252660 A1 | * | 10/2009 | Olver | C10G 9/20 422/600 |
| 2011/0171063 A1 | | 7/2011 | Lepez | |
| 2013/0247454 A1 | * | 9/2013 | Laska | C07C 2/00 44/457 |
| 2014/0239232 A1 | * | 8/2014 | Staton | G01N 31/12 252/373 |
| 2015/0275108 A1 | * | 10/2015 | Gueh | C10J 3/57 252/373 |

\* cited by examiner

CRACKING FURNACE

The invention relates to a cracking furnace for treating a gas, and particularly, but not exclusively, a gas coming from heat treatment of waste and/or biomass. The invention also relates to an assembly including such a cracking furnace and to a device for applying heat treatment to biomass and/or waste and that has an outlet that is connected to the inlet of said cracking furnace.

Biomass may comprise biodegradable fractions of substances, waste, and residues coming from agriculture, sylviculture, and from associated industries, with in particular biomass of vegetable origin, or solid portions of sludge from sewage treatment works, as well as biodegradable fractions of industrial and municipal waste. Waste may comprise industrial waste, in particular polymer waste (plastics materials, rubber, . . . ).

TECHNOLOGICAL BACKGROUND

For economical and ecological purposes, it is more and more common to treat biomass and/or waste with a view to obtaining combustible matter (solid, liquid, or gas) for energy purposes.

By way of example, it has been proposed to recycle biomass and/or waste by transforming it into gas that can be used by a gas engine. To this end, heat treatment (pyrolysis, gasification . . . ) of the biomass and/or of the waste makes it possible to recover a high-energy gas. However, the gas recovered in that way is too polluted by tar or oil phases to be used in risk-free manner by a gas engine.

In order to mitigate that drawback, it is known to follow the step of heat treating biomass and/or waste with a cracking step. That makes it possible to crack the tar and the oil phases so as to recover, at the end of the cracking step, a gas that is clean enough to be used by a gas engine (possibly after one or more additional purification steps concerning unwanted components other than the tar and oil phases).

By way of example, it has been proposed to implement the cracking step by means of a plasma torch. However, such a solution is relatively costly.

Thus, a less costly solution has been proposed that consists in causing the gas for treatment to flow in a pipe passing through an enclosure that is internally heated by means of a heating gas. Indirect heating of the pipe by the heating gas thus gives rise to a cracking reaction that cracks the tar and oil phases contained in the gas.

Nevertheless, is has been observed that such a solution does not enable the tar and oil phases of the gas for treatment to be purified very thoroughly.

OBJECT OF THE INVENTION

An object of the invention is to propose a cracking furnace for enabling better elimination of the tar and/or oil phases contained in a gas for treatment. An object of the invention is also to provide an assembly including such a cracking furnace and a device for applying heat treatment to biomass and/or waste and that has an outlet that is connected to the inlet of said cracking furnace.

GENERAL DEFINITION OF THE INVENTION

The above-mentioned problem is resolved in accordance with the invention by means of a cracking furnace comprising both a vertical tubular enclosure that includes an inlet for introducing a gas for treatment and an outlet for discharging said gas from the enclosure, and also means for heating said gas that comprise a heater tube extending vertically inside the enclosure and coaxially with the enclosure, the heater tube being shaped so as to have its bottom end closed and being arranged so that its bottom end is arranged in the enclosure and so that its top end is connected to a burner of the heater means, which heater means are arranged outside the enclosure.

Thus, the particular arrangement of the enclosure and of the heater tube makes it possible to create a treatment zone in which the gas is well confined. This makes it possible, within the enclosure, to promote heat exchange between the gas for treatment and the heater tube: cracking of the tar and oil phases is thus efficient and fast, in such a manner that the gas recovered at the outlet of the cracking furnace presents high purity.

In particular, when the gas for treatment is a gas coming from heat treatment (pyrolysis, gasification . . . ) of biomass and/or waste, the gas recovered at the outlet of the cracking furnace of the invention is sufficiently free from tar and oil phases to be used in a gas engine.

Naturally, in the present application the terms "top", "bottom", "horizontal", and "vertical", . . . should be understood relative to the direction of use of the cracking furnace, i.e. when the burner is arranged directly above the rest of the enclosure.

In the present application, the term "ceramic" should be understood as being a material that is refractory and inert (i.e. that is insensitive or that is only slightly sensitive to being in contact with a gas for treatment, even a corrosive gas), said material being manufactured and inorganic. A metal or an alloy is therefore not a ceramic in the meaning of the invention, and neither is a concrete.

The invention also relates to an assembly including such a cracking furnace as described above and a device for applying heat treatment to biomass and/or waste and that has an outlet that is connected to the inlet of said cracking furnace.

Other characteristics and advantages of the invention appear more clearly in the light of the following description and accompanying drawings, relating to particular embodiments of the invention.

BRIEF DESCRIPTION OF THE DRAWING

Reference is made to the accompanying figures, in which.

DETAILED DESCRIPTION OF PARTICULAR EMBODIMENTS OF THE INVENTION

Figures 1, 2:
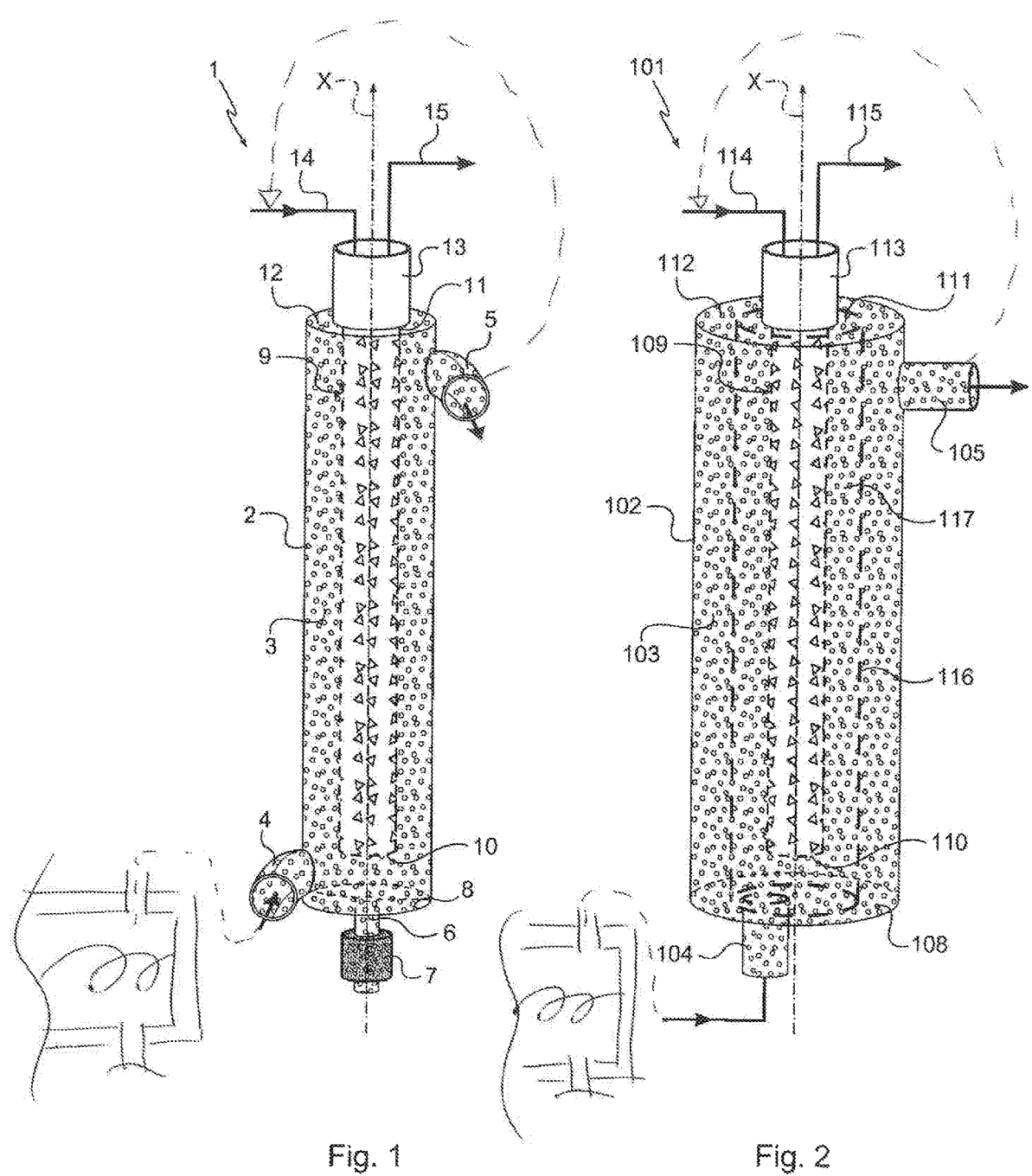
FIG. 1 is a diagrammatic view of a cracking furnace in a first embodiment of the invention.
FIG. 2 is a diagrammatic view of a cracking furnace in a second embodiment of the invention.

With reference to FIG. 1, the cracking furnace of the first embodiment of the invention, given overall reference 1, comprises an enclosure 2.

Preferably, the cracking furnace 1 enables a gas (represented by circles in FIG. 1) coming from heat treatment of biomass and/or waste (e.g. pyrolysis or gasification) to be subjected to a cracking step, said gas including tar and oil phases to be eliminated by said cracking step. In this embodiment, the cracking furnace is therefore shaped so as to subject the gas to a temperature lying in the range 900 degrees Celsius (° C.) to 1500° C., and preferably in the range 1000° C. to 1300° C. The cracking furnace 1 is preferably shaped to subject the gas to a temperature of about 1100° C. In addition, in this embodiment the cracking furnace 1 is shaped so that the gas passes through the enclosure 2 with a short transit time (typically lying in the range 0.5 seconds (s) to 2 s).

The enclosure 2 is shaped as a tubular enclosure 2 of vertical axis X. In this embodiment, the enclosure 2 is also shaped so as to be of circular section (section having as its normal the axis X).

The enclosure 2 includes an inlet 4 for introducing the gas for treatment. In this embodiment the inlet 4 is connected to the device for applying heat treatment to the biomass and/or the waste that has served to generate said gas for treatment. By way of example, such a device comprises a housing together with means for conveying the biomass and/or the waste between the inlet and the outlet of the housing, which means comprise a screw mounted to rotate in the housing about an axis of rotation and rotary drive means for rotating the screw, the device further comprising heater means for heating the screw by the Joule effect. In particular, such a device is described in documents WO 99/39549 and FR 2 892 888.

The enclosure 2 further includes an outlet 5 via which the gas is discharged. The inlet 4 is arranged in the bottom portion of the enclosure 2 and the outlet 5 is arranged in the top portion of the enclosure. In particular manner, the inlet 4 extends substantially tangentially to the enclosure 2. The inlet 4 is thus arranged so as to cause the gas to penetrate into the enclosure 2 along the inside wall of the enclosure 2. This makes it possible to generate a cyclone effect so that the gas flows helically in the enclosure 2. This enhances treatment of the gas.

Preferably, the outlet 5 is also arranged tangentially to the enclosure 2. Preferably, the inlet 4 and the outlet 5 are arranged relative to the enclosure 2 in directions that are opposite to each other in the radial direction, so as to facilitate the flow of gas for treatment throughout the entire enclosure 2.

In preferred manner, the enclosure 2 is made of refractory material. The inside walls of the enclosure 2 thus present good thermal radiation properties. In this example, more precisely, the enclosure 2 is made of ceramic. The ceramic selected for the enclosure 2 preferably presents a heat flux density lying in the range 10 kilowatts per square meter ($kW/m^2$) to 50 $kW/m^2$. By way of example, the ceramic selected is alumina. The cracking furnace 1 further comprises means for removing unwanted solid particles, such as dust, contained in the gas for treatment. To this end, in this embodiment, the removal means comprise a removal pipe 6 and a valve 7, e.g. of the rotary slide, guillotine, or clamshell type, arranged in said removal pipe 6. The valve 7 makes it possible to ensure sealing of the enclosure 2 so as to limit the entry of oxygen via the removal pipe 6 into the enclosure 2, which oxygen could hamper cracking. In this embodiment, the removal pipe 6 extends from the bottom wall 8 of the enclosure 2 to the outside of the enclosure 2. In this embodiment, the removal pipe 6 is arranged so as to open out at an end that is substantially in the center of said bottom wall 8 in the enclosure 2. In this embodiment, the removal pipe 6 extends along the axis X.

It therefore suffices merely to open the valve 7 in order to allow the unwanted solid particles to fall out of the enclosure 2. Preferably, the bottom wall 8 of the enclosure 2 is concave so as to form a funnel enabling not only better storage of the unwanted solid particles but also easier removal of the particles via the removal pipe 6 opening out into the funnel.

In addition, the cracking furnace 1 includes means for heating said gas for treatment, which means comprise in particular a heater tube 9. The heater tube 9 is shaped so as to extend vertically along the axis X in the enclosure 2, coaxially inside said enclosure 2. In this embodiment, the heater tube 9 is also shaped so as to be of circular section (section having as its normal the axis X). Thus, the enclosure 2 and the heater tube 9 together define an inside space of the annular section (section having as its normal the axis X) forming a treatment zone 3 for treating the gas. In addition, the heater tube 9 is shaped so that its bottom end 10 is closed and arranged inside the enclosure 2 without however touching the bottom wall 8 of the enclosure 2. This facilitates deposition of the unwanted solid particles on the bottom wall 8 of the enclosure 2, thus facilitating their removal.

However, the heater tube 9 presents a height, taken along the axis X, close to that of the enclosure 2, typically lying in the range 90% to 99% of the height of the enclosure 2. The top end 11 of the heater tube opens out from the enclosure 2, above the roof 12 of the enclosure 2.

In preferred manner, the heater tube 9 is made of ceramics. The ceramic selected preferably presents a heat flux density lying in the range 10 $kW/m^2$ to 50 $kW/m^2$. By way of example, the ceramic selected is alumina.

The heater means further comprise an inlet pipe 14 for a heating fuel (natural gas, fuel, purified synthesis gas, or also gas treated by the present cracking furnace 1, with a portion of the gas being taken from the outlet 5 of the cracking furnace 1 in order to feed the inlet pipe 14 . . . ) connected to a burner 13 of said heater means, which burner 13 is itself connected to the top end 11 of the heater tube 9. The heater means also comprise an outlet pipe 15 for the burnt fuel, which outlet pipe is also connected to the top end 11 of the heater tube 9.

Preferably, the heater means make use initially of an external heating fuel outside the cracking furnace 1 in order to initiate heating of the heater tube 9 (which fuel is of the natural gas, fuel oil, or purified synthesis gas type), and once treatment of the gas has commenced, the heater means take a portion of the treated gas from the outlet 5 of the cracking furnace 1 in order to heat the heater tube 9.

Thus, the cracking furnace 1 is relatively independent and requires an external fuel only for initializing the start of cracking.

The external fuel could also be used in operation, when merely taking treated gas from the outlet 5 of the cracking furnace 1 is not sufficient for powering the burner.

In operation, the gas for treatment is introduced into the enclosure 2 via the inlet 4. At the same time, the burner 13 burns the heating fuel thereby discharging a heating gas (represented by triangles in FIG. 1) into the heater tube 9. Said heating gas thus descends in the heater tube 9 before naturally rising to the top end 11 of the heater tube 9 where it is exhausted by the outlet pipe 15 to the outside of the cracking furnace 1. The presence and the movement of heating gas make it possible to heat the heater tube 9 efficiently over all of its height, which leads to the treatment zone 3 being heated by convection (at the heater tube 9) and by radiation (via the particular material constituting the enclosure 2). The gas for treatment is therefore heated efficiently, quickly, and uniformly up to the temperature required for thermal cracking of the oils and tar present in said gas, and in this embodiment up to a temperature of about 1100° C. This therefore gives rise to cracking of the harmful elements such as tar and/or oil phases present in said gas for treatment.

The gas for treatment flows naturally, and advantageously in helical manner by means of the cyclone effect caused by the tangential arrangement of the inlet 4, inside the enclosure 2 between the bottom inlet 4 of the enclosure 2 and the top outlet 5 of the enclosure through the entire treatment zone 3, which leaves time for the gas for treatment correctly before being discharged from the enclosure 2 at the outlet 5.

It should therefore be observed that the gas for treatment is heated indirectly since there is no physical contact between the heating gas or the fuel and the gas for treatment: only the heater tube 9 and the refractory inside walls of the enclosure 2 serve to heat the gas for treatment.

The particular configuration of the enclosure 2 and of the associated heater tube 9 thus makes it possible to define a narrow treatment zone 3 in which the gas for treatment is confined as it travels along the entire length of the enclosure 2, the treatment zone 3 being heated externally by inside refractory walls of the enclosure 2 and being heated internally by the heater tube 9. This makes it possible to obtain uniform heating of the gas for treatment throughout the entire treatment zone, thus ensuring good cracking of the undesirable tar and oil phases.

With reference to FIG. 2, a second embodiment of the invention is described below. Elements that are shared with the first embodiment have the same numerical references plus 100.

In this second embodiment, the removal means for removing unwanted solid particles no longer include a removal pipe and an associated valve, but rather a filter 116 extending vertically along the axis X inside the enclosure 102, coaxially between said enclosure 102 and the heater tube 109, in such a manner that the heater tube 109 extends inside the filter 116, which is inside the enclosure 102. In this embodiment, the filter 116 is also shaped so as to be of circular section (section having as its normal the axis X). The filter 116 has a height equal to that of the enclosure 102 so as to be secured firstly to the roof 112 of the enclosure 102 and secondly to the bottom wall 108 of the enclosure.

Thus, the enclosure 102 and the heater tube 109 still define between them an inside space forming a treatment zone 103 for treating the gas, but the filter 116 and the heater tube 109 further define between them a filtering zone 117 for filtering the gas.

By way of example, the filter 116 is made of ceramics.

In this embodiment, the inlet 104 of the enclosure 102 is shaped so as to open out directly into said zone 117 for filtering the gas. To this end, the inlet 104 opens out in the bottom wall 108 of the enclosure 102 into said filtering zone 117. As for the outlet 105, it is shaped so as to open out into the treatment zone 103 but outside the filtering zone 117.

Thus, when in operation, the gas for treatment is introduced into the enclosure 102 via the inlet 104 so as to flow into the enclosure 102 inside the filtering zone 117. At the same time, the burner 113 burns the fuel that discharges a heating gas into the heater tube 109. Said heating gas thus descends in the heater tube 109 before naturally rising to the top end 111, where it is exhausted by the outlet pipe 115 to the outside of the cracking furnace 101. The presence and the movement of heating gas make it possible to heat the heater tube 109 efficiently over all of its height, which leads to the treatment zone 103 being heated by convection (at the heater tube 109) and by radiation (via the particular material constituting the enclosure 102). This therefore gives rise to cracking of the harmful elements such as tar and/or oil phases present in said gas for treatment. The gas for treatment flows naturally inside the enclosure 102 between the bottom inlet 104 of the enclosure 102 and the top outlet 105 of the enclosure throughout the entire treatment zone 103. Furthermore, such natural movement forces the gas to pass through the filter 116 in order to rise up to the outlet 105. Although the filter 116 allows said gas to pass through, in contrast it retains the unwanted solid particles, thereby enabling not only tar and oil phases, but also unwanted solid particles to be cleaned from the gas that leaves via the outlet 105.

The invention is not limited to the embodiments described but, on the contrary, encompasses any variant coming within the ambit of the invention.

Naturally, the cracking furnace of the invention could be used for treating gas of types other than those coming from heat treatment of biomass and/or waste. However, the cracking furnace of the invention is particularly adapted to gas coming from heat treatment of biomass and/or waste.

Although in the above description the tubular enclosure is of circular section, the enclosure could present a section that is different, such as an elliptical section. However, it is preferable to have an enclosure of circular section since that promotes heat exchange within the treatment zone. In addition, the heater tube could have a section that is different from a circular section, such as an elliptical section. However, it is preferable to have a heater tube of circular section, since that promotes heat exchange within the treatment zone. In any event, a cracking furnace is preferred in which the heater tube and the enclosure have sections of the same shape, since that promotes heat exchange within the treatment zone.

Although in this example the enclosure is made of alumina, the enclosure could be made of any other material: another ceramic, a refractory concrete, a metal, or a metal alloy . . . . However, preference is given to refractory materials such as refractory concrete or ceramics that enhance the treatment of the gas. Furthermore, the nature of the gas for treatment (in particular, whether it is corrosive or not) is also taken into consideration.

In addition, although in this example the heater tube is made of alumina, the heater tube could be made of any other material: another ceramic, a refractory concrete, a metal, or a metal alloy . . . . However, preference is given to refractory materials such as refractory concrete or ceramics that enhance the treatment of the gas. Furthermore, the nature of the gas for treatment (in particular, whether it is corrosive or not) is also taken into consideration.

In addition, although in this example the heater tube is made of alumina, the filter could be made of any other material: another ceramic, a refractory concrete, a metal, or a metal alloy . . . . However, preference is given to refractory materials such as refractory concrete or ceramics that enhance the treatment of the gas. Furthermore, the nature of the gas for treatment (in particular, whether it is corrosive or not) is also taken into consideration.

The outlet of the cracking furnace could be combined with other additional means for eliminating the impurities present in the gas and/or with gas purification means.

The invention claimed is:
1. A cracking furnace comprising:
a vertical tubular enclosure comprising:
an inlet for introducing a gas for treatment; and
an outlet for discharging said gas from the enclosure; and
means for heating said gas that comprise:
a burner arranged outside the vertical tubular enclosure;
a heater tube extending vertically inside the vertical tubular enclosure and coaxially with the vertical tubular enclosure, the heater tube comprising:

a closed bottom end closed arranged inside the vertical tubular enclosure;

a top end is connected to the burner, wherein the inlet is arranged to cause the gas for treatment to penetrate into the vertical tubular enclosure along an inside wall of the vertical tubular enclosure in order to generate a cyclone effect so that the gas flows helically in the vertical tubular enclosure.

2. The cracking furnace according to claim 1 wherein the vertical tubular enclosure is shaped so as to be of circular cross-section.

3. The cracking furnace according to claim 1 wherein the heater tube is shaped so as to be of circular cross-section.

4. The cracking furnace according to claim 1 wherein the heater tube is made from ceramics.

5. The cracking furnace according to claim 1 wherein at least one of the inside walls of the vertical tubular enclosure is made of refractory material.

6. The cracking furnace according to claim 5, wherein the refractory material is made from ceramics.

7. The cracking furnace according to claim 6, wherein the ceramics include alumina.

8. The cracking furnace according to claim 5, wherein the refractory material is made from concrete.

9. The cracking furnace according to claim 1 further comprising removal means for removing unwanted solid particles contained in the gas for treatment.

10. The cracking furnace according to claim 9, wherein said removal means comprise:

a removal pipe extending from a bottom wall of the vertical tubular enclosure towards the outside of the vertical tubular enclosure; and a valve arranged in said removal pipe.

11. The cracking furnace according to claim 10, wherein the bottom wall of the vertical tubular enclosure is concave so as to form a funnel.

12. The cracking furnace according to claim 9, wherein said removal means comprise a filter extending vertically inside the vertical tubular enclosure, coaxially with said vertical tubular enclosure and with the heater tube, so that the heater tube extends inside the filter inside the vertical tubular enclosure.

13. The cracking furnace according to claim 12, wherein the filter is made from ceramics.

14. The cracking furnace according to claim 1 wherein the heater means are shaped to take a portion of the gas from the outlet of the cracking furnace in order to feed the burner.

15. An assembly comprising:

a cracking furnace according to claim 1 and a device for applying heat treatment to biomass and/or waste and that has an outlet that is connected to the inlet of the cracking furnace.

16. The assembly according to claim 15, wherein the device for applying heat treatment comprises a housing together with means for conveying the biomass and/or the waste between the inlet and the outlet of the housing, which means comprise a screw mounted to rotate in the housing about an axis of rotation and rotary drive means for rotating the screw, the device further comprising heater means for heating the screw by the Joule effect.

17. A cracking furnace comprising:

a vertical tubular enclosure comprising:

an inlet for introducing a gas for treatment; and an outlet for discharging said gas from the enclosure;

means for heating said gas that comprise:

a burner arranged outside the vertical tubular enclosure; and a heater tube extending vertically inside the vertical tubular enclosure and coaxially with the vertical tubular enclosure, the heater tube comprising:

a closed bottom end closed arranged inside the vertical tubular enclosure; and a top end is connected to the burner; and removal means for removing unwanted solid particles contained in the gas for treatment, said removal means comprising a filter extending vertically inside the vertical tubular enclosure, coaxially with said vertical tubular enclosure and with the heater tube, so that the heater tube extends inside the filter inside the vertical tubular enclosure.

18. The cracking furnace according to claim 17, wherein the vertical tubular enclosure is shaped so as to be of circular cross-section.

19. The cracking furnace according to claim 17, wherein the heater tube is shaped so as to be of circular cross-section.

20. The cracking furnace according to claim 17, wherein the inlet is arranged to cause the gas for treatment to penetrate into the enclosure along an inside wall of the enclosure.

21. The cracking furnace according to claim 17, wherein the heater tube is made from ceramics.

22. The cracking furnace according to claim 17, wherein at least one of the inside walls of the vertical tubular enclosure is made of refractory material.

23. The cracking furnace according to claim 22, wherein the refractory material is made from ceramics.

24. The cracking furnace according to claim 23, wherein the ceramics include alumina.

25. The cracking furnace according to claim 22, wherein the refractory material is made from concrete.

26. The cracking furnace according to claim 17, wherein said removal means comprise:

a removal pipe extending from a bottom wall of the vertical tubular enclosure towards the outside of the vertical tubular enclosure; and a valve arranged in said removal pipe.

27. The cracking furnace according to claim 26, wherein the bottom wall of the vertical tubular enclosure is concave so as to form a funnel.

28. The cracking furnace according to claim 17, wherein the filter is made from ceramics.

29. The cracking furnace according to claim 17, wherein the heater means are shaped to take a portion of the gas from the outlet of the cracking furnace in order to feed the burner.

30. An assembly comprising:

a cracking furnace according to claim 17; and a device for applying heat treatment to biomass and/or waste and that has an outlet that is connected to the inlet of the cracking furnace.

31. The assembly according to claim 30, wherein the device for applying heat treatment comprises a housing together with means for conveying the biomass and/or the waste between the inlet and the outlet of the housing, which means comprise a screw mounted to rotate in the housing about an axis of rotation and rotary drive means for rotating the screw, the device further comprising heater means for heating the screw by the Joule effect.

* * * * *